United States Patent
Obremski et al.

(10) Patent No.: US 7,157,234 B2
(45) Date of Patent: Jan. 2, 2007

(54) DETECTION OF VERY LOW QUANTITIES OF ANALYTE BOUND TO A SOLID PHASE

(75) Inventors: Robert J. Obremski, Yorba Linda, CA (US); John W. Silzel, Yorba Linda, CA (US); Tsong-Tseh Tsay, Orange, CA (US); Bibijana Cercek, Yorba Linda, CA (US); Charles L. Dodson, Orange, CA (US); Tung Rung Wang, Fullerton, CA (US); Yagang Liu, Irvine, CA (US); Zhou Shaomin, Yorba Linda, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/063,978

(22) Filed: Apr. 21, 1998

(65) Prior Publication Data

US 2002/0001853 A1    Jan. 3, 2002

Related U.S. Application Data

(60) Provisional application No. 60/065,937, filed on Oct. 24, 1997.

(51) Int. Cl.
 G01N 33/53 (2006.01)
 G01N 33/537 (2006.01)
 G01N 33/543 (2006.01)
 C12Q 1/00 (2006.01)
 C12N 13/00 (2006.01)

(52) U.S. Cl. .......................... 435/7.1; 435/4; 435/7.92; 435/7.93; 435/7.94; 435/7.95; 435/174; 435/283.1; 435/287.1; 435/287.2; 435/287.7; 435/288.3; 435/402; 436/501; 436/502; 436/506; 436/507; 436/543; 436/546

(58) Field of Classification Search .......... 250/440.11; 378/44, 47, 79; 435/71, 7.93, 7.94, 7.95, 435/960, 4, 7.1, 174, 283.1, 287.1, 287.2, 435/287.7, 287.9, 288.3, 402, 7.92; 436/25, 436/36, 501, 512, 546, 506, 507, 543, 807, 436/808, 809, 502

See application file for complete search history.

(56) References Cited

U.S. PATENT DOCUMENTS

| 4,385,126 A | 5/1983 | Chen et al. .................. 436/518 |
| 4,745,072 A * | 5/1988 | Ekins et al. ................. 436/500 |

(Continued)

FOREIGN PATENT DOCUMENTS

EP    134215    * 8/1983

(Continued)

OTHER PUBLICATIONS

Ekins et al. 1989. J. of Biolum and Chemilum. 4:59-79.*

(Continued)

*Primary Examiner*—Lynette R. F. Smith
*Assistant Examiner*—J. Hines
(74) *Attorney, Agent, or Firm*—Hogan & Hartson LLP

(57) ABSTRACT

A microscale binding assay, analyte binding array, and kits are disclosed, which exploit the mass action law to harvest analyte from a liquid sample. This is achieved by fabrication of sorbent zones having up to ten times the binding capacity per unit area generally obtained on polystyrene microtiter plates. The resulting arrays substantially deplete the liquid solution of analyte during incubation. Accordingly, the assays respond to total mass of analyte in the sample, not analyte concentration. This approach, coupled with direct fluorescence detection in the NIR, yields maximal signal intensity and low background for optimal sensitivity.

42 Claims, 7 Drawing Sheets

U.S. PATENT DOCUMENTS

| | | | | |
|---|---|---|---|---|
| 4,954,435 | A | | 9/1990 | Krauth ............................ 435/7 |
| 5,171,695 | A | | 12/1992 | Ekins .......................... 436/501 |
| 5,268,486 | A | * | 12/1993 | Waggoner et al. .......... 548/427 |
| 5,432,099 | A | | 7/1995 | Ekins .......................... 436/518 |
| 5,453,505 | A | * | 9/1995 | Lee et al. .................... 544/124 |
| 5,512,659 | A | * | 4/1996 | Ullman et al. ........... 530/391.1 |
| 5,516,635 | A | * | 5/1996 | Ekins et al. .................... 435/6 |
| 5,639,423 | A | * | 6/1997 | Northrup et al. ............. 122/50 |

FOREIGN PATENT DOCUMENTS

| | | | |
|---|---|---|---|
| EP | 271974 | * | 8/1987 |
| EP | 304202 | * | 8/1988 |
| EP | 0 134 215 B1 | | 10/1989 |
| EP | 0 304 202 B1 | | 7/1992 |
| EP | 0 271 974 B1 | | 3/1993 |
| WO | WO 84/01031 | | 3/1984 |
| WO | WO 88/01058 | | 2/1988 |
| WO | WO 89/01157 | | 2/1989 |
| WO | WO 93/08472 | | 4/1993 |
| WO | WO 95/18376 | | 7/1995 |
| WO | WO 95/18377 | | 7/1995 |
| WO | WO 95/24649 | | 9/1995 |
| WO | WO 95/35505 | | 12/1995 |
| WO | WO 9732212 | | 9/1997 |

OTHER PUBLICATIONS

Ekins et al. 1990. Ann. Biol. Clin. 48:655-666.*

Ekins et al. 1990. J. of Clin. Immuno. 13(4):169-181.*

Ekins et al. 1989. Analytica Chimica Acta. 73-96.*

Ekins, Rober et al; "Development of Microspot Multi-Analyte Ratiometric Immunoassay Using Dual Fluorescent-Labelled Antibodies" Analytica Chimica Acta 227 (1989).

Ekins, R. et al; "Multianalyte Microspot Immunoassay, The Microanalytical 'compact disk' of the Future", Ann Biol Clin, V. 50, pp. 337-353 (1992).

Kakabakos, S. et al; Multianalyte Immunoassay Based on Spatially Distinct Fluorescent Areas Quantified by Laser-Excited Solid-Phase Time Resolved Fluorometry; Clin. Chem. 38/3, pp. 338-342 (1992).

Sigal, Nolan et al; "Approaches and Technologies for Screening Large Combinatorial Libraries"; Combinatorial Chemistry and Molecular Diversity in Drug Discovery, pp. 433-443 (1998).

Ekins, R.P., et al., "Developing multianalyte assays", Reviews—*Trends in Biotechnology*, p. 89 (1992).

Ekins, R., et al., "High specific Activity Chemiluminescent and Fluorescent Markers: their Potential Application to High Sensitivity and 'Multi-analyte' Immunoassays", *J. of Bioluminescence and Chemiluminescence*, 4:59 (1989).

Ekins, R., et al., "Development of Microspot Multi-Analyte Ratiometric Immunoassay Using Dual Fluorescent-Labelled Antibodies", *Analytica Chimica Acta*, 227:73 (1989).

Ekins, R.P., "Multi-analyte immunoassay", *Journal of Pharmaceutical & Miomedical Analysis*, 7(2):155 (1989).

Ekins, R., et al., "Fluorescence spectroscopy and its application to a new generation of high sensitivity, multi-microspot, multianalyte, immunoassay", *Clinica Chimica Acta*, 194:91 (1990).

Ekins, R., et al., "Multispot, multianalyte, immunoassay", *Ann. Biol. Clin.*, 48:655 (1990).

Ekins, R., "Time resolved fluorescenct spectroscopy and its application to a new generation of high sensitivity, muti analyte, 'microspot' immunoassays" *Fresenius J. Anal. Chem.*, 337:20 (1990).

Ekins, R.P., et al., "Multianalyte Immunoassay: The Immunological 'Compact Disk' of the Future", *J. Clin. Immunoassay*, 13(4):169 (1990).

Ekins, R.P., "Competitive, Noncompetitive, and Multi-Analyte Microspot Immunoassays", *Immunochemistry of Solid-Phase Immunoassay*, Chapt. 6, p. 105 (1991).

Ekins, R.P., et al., "Multianalyte Microspot Immunoassay-Microanalytical 'Compact Disk' of the Future", *Clin. Chem.*, 37(11):1955 (1991).

Ekins, R., "Principles of Non-Competitive Methods", *Principles of Immunoassays*, Chapt. 3.3.2, Pub.: VCH, New York, p. 227 (1993).

Ekins, R., et al., "Multianalyte Testing[Letter]", *Clin. Chem.*, 39(2):369 (1993).

Ekins, R.P., "New perspectives in radioimmunoassay", *Nuclear Medicine Communications*, 14:721 (1993).

Ekins, R., et al., "Multianalyte Microspot Immunoassay", *Anal. Proc.*, 30:488 (1993).

Ekins, R., "Immunoassay: recent developments and future directions", *Nucl. Med. Biol.*, 21(3):495 (1994).

Kakabakos, S.E., et al., "Multianalyte Immunoassay Based on Spatially Distinct Fluorescent Areas Quantified by Laser-Excited Solid-Phase Time-Resolved Fluorometry", *Clin. Chem.*, 38 (3):338 (1992).

Patel, N., "Application of Ambient Analyte Immunoassays for Pesticide Multi-Residue Analysis", Proceedings of *Food Safety and Quality Assurance: Applications of Immunoassay Systems*, Ed. M.R.A. Morgan; Elsevier Applied Science, London/New York, p. 129 (1991).

Brett a. Stillman et al.; *Expression Microarray Hybridization Kinetics Depend on Length of the Immobilized DNA but Are Independent of Immobilization Substrate*; Analytical Biochemistry, 295; 149-157 (2001).

Kim E. Sapsford et al.; *Kinetics of Antigen Binding to Arrays of Antibodies in Different Sized Spots*; Anal. Chem. 2001, 73, 5518-5524.

* cited by examiner

DETECTION OF VERY LOW QUANTITIES OF ANALYTE BOUND TO A SOLID PHASE

RELATED APPLICATIONS

The present application is related to co-pending provisional application Ser. No. 60/065,937, filed Oct. 24, 1997, entitled "Method for Quantitative Analysis of Image Data from Ligand Binding Assays," by inventors Robert J. Obremski, John W. Silzel, and Tsong-Tseh Tsay. This application is incorporated herein by reference.

FIELD OF THE INVENTION

The field of the invention is ligand binding assays in which the analyte is detected and quantified, directly or indirectly, on the basis of its specific affinity for a chemically modified solid material.

BACKGROUND

The ability to perform chemical measurements in microscopic volumes has many applications in analytical chemistry. This is particularly true for the broad group of heterogeneous "ligand binding assays." This broad class includes hybridization assays for specific DNA sequences, immunoassays employing immobilized antigen or antibody, and the receptor assays used in high throughput screening of pharmaceuticals.

When such assays are "scaled down" to the microscopic level, there is a clear reduction in the cost per test, related to the use of smaller quantities of the "sorbent" materials—the specific antibodies, nucleic acid probes, or receptor molecules employed. Because these reagents must often have exquisite selectivity for the analyte, while remaining inert to other sample constituents, they often represent a large fraction of the total reagent cost in conventional assay methods. In addition to the scale-related reduction of cost, micro-scale methods may facilitate parallel testing for multiple analytes in a single sample. Scaling down permits multiple tests to be probed optically within the constraints of conventional optical systems.

The theory of microscopic assay has been advanced by the work of Ekins et al. {"Multianalyte Microspot Immunoassay—Microanalytical "Compact Disc" of the Future," *Clin. Chem* 37(11), 1955–1967 (1991); "Development of Microspot Multi-Analyte Ratiometric Immunoassay using Dual Fluorescent-Labelled Antibodies," Anal. Chim. Act. 227, 73–96 (1989)}, which has focused on the concept of "ambient analyte" assay. Under ambient analyte conditions, the equilibrium number of analyte molecule bound by the solid phase is minimal relative to the number of analyte molecules present in solution. Such a regime minimally perturbs the analyte concentration in the solution over the solid phase during the course of an assay. This approach has the theoretical advantage of perturbing minimally any equilibria between the analyte and other sample constituents. For example, in a diagnostic assay it may be desirable to determine the concentration of a "free" drug molecule in the presence of an albumin-bound form without pertubing the physiological equilibrium of the sample. The "ambient analyte" assay also has the advantage of requiring minimal mass transport from solution to the surface, and so makes minimal demands on the kinetics of transport from bulk solution to a microscopic region bearing capture reagent.

Ambient analyte assays have been modeled by Ekins et al. using the mass action law and chemical activities computed by dividing the amount of analyte binding sites provided on the solid support into the total liquid reagent volume. With these assumptions, "ambient analyte assay" conditions are said to exist if the binding site "activity" is <0.01 $K^{-1}$, where K is the ligand binding affinity in liter $mole^{-1}$. Ekins et al. point out that reducing the area of the solid phase employed in an assay reduces also the background signals, which often limit the sensitivity of ligand binding assays. Although the "ambient analyte" approach tends to reduce signal by reducing the amount of analyte bound, the background reduction afforded by the use of microscopic solid phase regions permits the overall signal to background ratio to remain favorable to high sensitivity.

The ambient analyte regime, by virtue of its low percent recovery of analyte, makes stringent demands on laser monochromaticity, optical filters, permissible stray light, and perhaps, most importantly, the permissible background from the solid phase itself. Moreover, the practical concerns of analyte concentration and sample volume limits the total number of analyte molecules available for detection. Indeed, for some micro-scale applications, the entire amount of analyte available in the sample may be barely sufficient for practical detection above background.

For the foregoing reasons there is a need for microscale assay methods having increased sensitivity for very low quantities of analyte. Preferably, the miniaturized binding assays will maximize the amount of analyte bound to a substrate for detection and quantification. Moreover, such scaled down binding assays should minimize the use of costly "sorbent materials' and permit more than one assay to be performed on the same sample volume.

SUMMARY

The present invention is directed to an assay method, an analyte binding array, and kits that satisfy the need for micro-scale binding assays having increased sensitivity for very low quantities of analyte.

The binding assay detects analyte mass rather than analyte concentration, in a liquid sample. An array of sorbent zones is immobilized on a substrate. The sorbent zones include an analyte binding partner, which can be an oligonucleotide probe, antibody, or receptor molecule. When a defined volume of sample, believed to contain an analyte, is deposited on a sorbent zone, the analyte is substantially depleted from the sample to form an analyte capture complex with the analyte binding partner. Analytes of interest can include polynucleotide molecules, antigens, haptens, drugs, and hormones. Generally, the analyte binding partner is present in molar excess relative to the analyte.

In one embodiment of the present invention, the sorbent zones also contain a first binding partner attached to the substrate, wherein the first binding partner forms a first binding complex with a conjugate. The conjugate comprises a first ligand and the analyte binding partner. The first ligand binds specifically with the first binding partner and the analyte binding partner can bind specifically with the analyte. A preferred embodiment utilizes avidin or steptavidin as the first binding partner, whereas the first ligand is biotin. A most preferred version uses biotinylated antibody as conjugate.

The immobilizing step can be conducted by dispensing droplets using a printer jet to form the array of sorbent zones, wherein the volume of the droplets is about 80 pl to about 1 nl. Preferably, the immobilization step also includes covalent attachment of a binding partner to the substrate.

The analyte capture complex is tagged with a fluorescent label and the sorbent zone is illuminated with a laser in the absence of liquid. The fluorescent labels are preferably carbocyanine dyes, such as Cy5, BCy5, DBCy5, Cy7, BCy7, and DBCy7. Moreover, the tagging step is preferably conducted by incubating the analyte capture complex with a labeled binding partner. The labeled binding partner has a fluorescent label, preferably a carbocyanine dye, and can also bind to the analyte capture complex. Most preferably, the labeled binding partner is an antibody.

The illuminating step is preferably conducted by directing near infrared emissions from a laser source through a prism coupler, into the substrate, thereby producing evanescent wave excitation of fluorescence. Fluorescence emissions are detected from any sorbent zone having an analyte capture complex tagged with a fluorescent label, thereby determining the analyte mass harvested from the defined volume of sample.

Preferred substrates are selected from the group consisting of polycarbonate, polystyrene, polyethylene, polypropylene, and polymethylmethacrylate. Moreover, the substrate can be in the form of a film, sheet, strip, or microtiter plate.

The assay can be optimized using a defined volume of sample from about 50 μl to about 500 μl. Preferably, the amount of the analyte binding partner immobilized in a sorbent zone is from $10^5$ to about $10^{12}$ molecules of analyte binding partner and the diameter of the sorbent zones is about 60 μm to about 500 μm. Under these conditions, about $10^5$ to about $10^{10}$ molecules of analyte can be detected per sorbent zone.

A most preferred version of the assay is a multianalyte assay, wherein the array of sorbent zones comprises a plurality of different analyte binding partners. The sorbent zones may also be subdivided into at least two subsets, wherein a first subset of sorbent zones contain a first analyte binding partner and a second subset of sorbent zones contain a second analyte partner.

For convenience, the present invention also provides for an analyte binding array, which can harvest analyte from a liquid sample for testing. Similarly, kits are provided with labeled binding partner in addition to the array.

DESCRIPTION OF THE DRAWINGS

These and other features, aspects, and advantages of the present invention will become better understood with regard to the following description, appended claims, and accompanying drawings where:

DETAILED DESCRIPTION

I. Introduction

Figure 1:
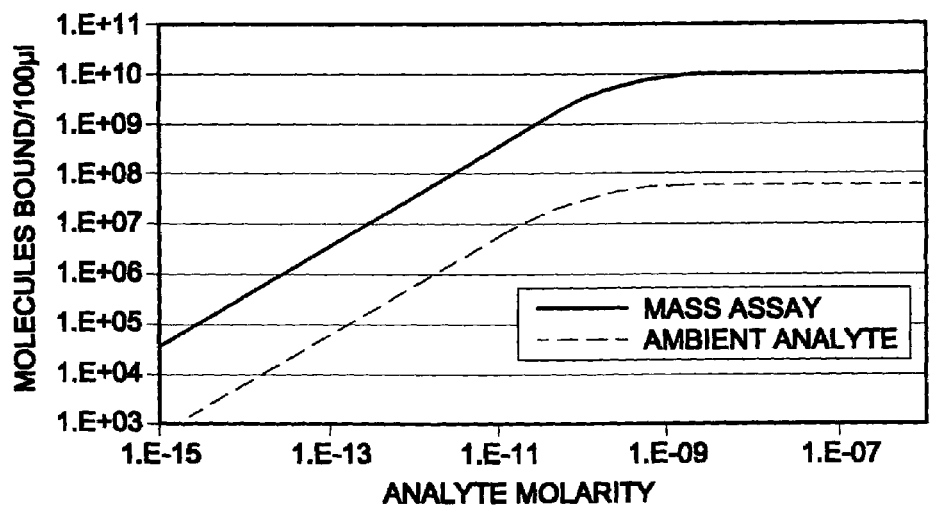
FIG. 1 shows the computed TSH assay equilibrium for "mass assay" and "ambient analyte assay" regimes (an antibody affinity of $10^{-10}$ liter mole$^{+1}$ and a volume of 100 μl are assumed; the mass assay assumes $10^{10}$ binding sites per 100 μl)

Reduction of size offers many anticipated advantages to analytical methods, such as reduced costs, faster chemistry, and equivalent or improved sensitivity. The present invention is directed to ligand binding assays in which the analyte is quantified, directly or indirectly, on the basis of its specific affinity for a chemically modified solid material. This broad class includes hybridization assays for specific DNA sequences, immunoassays employing immobilized antigen or antibody, and the receptor assays used in high throughput screening of pharmaceuticals. In addition to the benefits noted above, the present invention provides a multianalyte capability with all analytes exposed to the solid phase simultaneously and measured simultaneously.

Our efforts in "scaling down" assay technologies arose out of a desire to maximize the useful analytical signal from any given assay system. Specifically, our experiments indicated that direct laser induced fluorescence (LIF) detection afforded greater dynamic range and simplicity than many assay detection methods involving enzyme amplification. Background fluorescence from biologicals, which often limits the sensitivity of direct fluorescence in the visible region, was largely circumvented in our laboratory by the use of fluorophores absorbing and emitting in the short wave near-infrared (NIR) region, where biologicals are more optically inert {Obremski, R. J., et al., "Near IR fluorescence: instrumentation, application, and pitfalls." In: Burgess, C., Jones, D. G., eds. Spectrophotometry, Luminescence and Colour; Science and Compliance. Amsterdam: Esevier, 1995:235–246}. Sensitivity using LIF in the NIR region was then limited principally by Raman scattering from the solvent (generally water), and by the optical considerations of achieving efficient excitation of a solution volume or solid phase having dimensions on the order of 0.5 to 1 cm.

A solution to these problems was envisioned in the placement of the entire solid phase "sorbent" for an assay in a microscopic volume, which could be efficiently probed by simple laser optics. Removing the solid phase from the liquid environment, and making our measurements in the absence of liquid would then eliminate solvent backgrounds. We anticipated, as have Ekins and Chu {"Multianalyte Testing [Letter]. Clin Chem 39:369–370 (1993)}, that the background fluorescence or scattering related to the solid phase itself would fall off as the viewed "sorbent" area was reduced. However, our use of the NIR largely reduces this background to the inevitable Raman scattering, and our overriding concern was the maximization of signal. To achieve this maximization, we have developed methods for preparing microscopic sorbent zones in an effort to maximally perturb the sample concentration by harvesting the entire analyte mass, to the extent possible, onto the microscopic measurement region. In our assay regime, therefore, the microscopic "sorbent" region acts as a sample concentration device. Unlike the "ambient analyte" regime of Ekins et al., which measures analyte concentration, our method detects instead the analyte mass present in the applied liquid volume. In theory, this mass assay regime would yield an equivalent response to a 100 ul sample containing $10^{-13}$M analyte or a 10 ul aliquot containing the same analyte at $10^{-12}$M. This presupposes equilibration of the capture reagent with the liquid bulk, which will be addressed in the experimental section.

II. Mass Assay Theory

Consider a TSH assay performed using the proposed "mass assay" method. It will be shown in the experimental section that our typical binding capacity in a single 150 micron sorbent zone is on the order of $10^{10}$ analyte molecules. If this zone were in contact with a 100 ul sample volume, the effective "concentration" of sorbent would be $1.7 \times 10^{-10}$M. Note that this is 1–2 decades higher than the $0.01 K^{-1}$ dictated by "ambient analyte" theory, since most optimized antibodies have K near $10^9$ or $10^{10}$.

$$K = \frac{xVN}{(Ab_o - x) \cdot (Ag - x)} \quad (1)$$

Consider equation (1) in which N is Avogadro's number and x represents the number of molecules of antigen-antibody complex present in a system of volume V at equilibrium, assuming an affinity constant K, with $Ab_o$ and $Ag_{o-}$ moles of antibody and antigen, respectively, present initially. Under "ambient analyte" conditions, the complex would have little effect on the concentration in solution and the variable x can be dropped in the terms of the denominator. Assuming $K = 10^{10}$ liter mole$^{-1}$, a volume of 100 microliters, and 60,000 molecules of TSH available for assay ($10^{-15}$ mole liter$^{-1}$), 600 molecules would be bound and provide signal. In the "mass assay" method, equation 1 must be solved in quadratic form, and it is found that at equilibrium, roughly 38,000 molecules of analyte are bound, over 60% of the total analyte mass available. The absolute fluorescence signal expected from the "mass assay" is 60 times that calculated from the guidelines proposed for "ambient analyte" conditions. The theoretical advantage in percent recovery is maintained at higher analyte concentrations, as indicated in FIG. 1.

Of course, these models and discussion are predicated on the assumption that chemical equilibrium can be reached in microscopic-scale ligand binding assays under reasonable conditions. The formulation of thermodynamic chemical activities in equation (1) using the total liquid volume clearly ignores the kinetic diffusive barrier between the bulk solution and a microscopic sorbent region, which must operate in any real system. Certainly the mass assay method calls for the minimization of the assay volume (by the avoidance of sample dilution) to facilitate maximum harvest of analyte.

III. Samples and Analytes

The binding assay of the present inventions can be adapted for use with a variety of liquid samples. Clinical samples, such as blood, serum, plasma, cerebrospinal fluid, or urine, are preferred. An analyte of interest that may be detected in the sample, is preferably a clinically relevant biomolecule capable of binding specifically with a binding partner, such as an oligonucleotide, antibody, or receptor molecule. Such analytes can include antigens, haptens, drugs, hormones and polynucleotides having specific nucleotide sequences that are complementary to particular oligonucleotide probes, antigens, haptens, drugs, and hormones. In preferred versions of the present invention, the analyte is an antigenic substance capable of binding specifically with a capture antibody.

IV. Substrate

The assay system of the present invention is conducted by first immobilizing "sorbent material" on a substrate or solid support. The solid support is preferably an insoluble nonporous plastic material or glass. Polystyrene is a preferred plastic material due to its optical transparency, high refractive index, and amenability to chemical coupling, but other polyolefins or acrylic or vinyl polymers could likewise be used. For instance, polycarbonate, polymethylmethacrylate, polyethylene, and polypropylene are all suitable. The substrate can be in the form of a film, sheet, or strip, which can be spotted with an array of droplets. Alternatively, the substrate can be particles or in a multiwell configuration, such as a microtiter plate, wherein liquid samples of defined volumes can be readily retained in spaced apart locations. When the illumination step of the assay is performed using evanescent wave excitation of fluorescence (explained in more detail below), the substrate is preferably a transparent material having a high refractive index, most preferably a refractive index higher than water.

IV. Sorbent Zones

The sorbent zones of the present invention are discrete regions on the substrate where sorbent materials are localized. The sorbent materials can include ligands that can bind specifically with a binding partner. For example, ligands can include oligonucleotides, haptens, antigens, drugs, hormones, or biotin. Moreover, sorbent materials can also include the corresponding binding partners that bind specifically to ligands and/or analytes. Accordingly, the binding parter of an oligonucleotide would be a nucleic acid having a complementary nucleic acid sequence. The binding partner of a drug or hormone could be a receptor molecule. A binding partner of biotin is avidin or streptavidin. Moreover, most ligands have corresponding antibody molecules that are specific binding partners.

Accordingly, the analyte binding partners will preferably be antibodies, more preferably monoclonal antibodies. Monoclonal antibodies to a wide variety of analytes are commercially available or may be made by known techniques. The antibodies used will generally have conventional affinity constants on the order of about $10^8$ to about $10^{11}$ liters/mole, however high affinity antibodies, having affinity constants of about $10^{12}$ to about $10^{13}$ can also be used.

In a preferred version of the present invention the sorbent zone includes a first binding partner and a conjugate. The first binding partner can be any of the binding partners listed above, but is most preferably avidin or streptavidin due to the high affinity binding (about $10^{15}$ liters/mole) of these sorbent materials with biotin. The conjugate is composed of a first ligand and an analyte binding partner. The first ligand can be any of the ligands listed above, depending on the first binding partner, but is most preferably biotin. Accordingly, a most preferred conjugate is a biotinylated antibody.

The dimensions of the sorbent zones is limited by the precision and accuracy of the method distributing zones in an array. However, the economical use of costly sorbent materials dictates keeping the size of sorbent zones to a minimum. Moreover, minimizing the size of a sorbent zone containing a fluorescent label unexpectedly increases the signal to noise ratio during image detection. As a practical matter, a droplet volume of around 80 picoliters of sorbent material can be dispensed with a precision of about 6% CV using thermal/piezo jet printing methods. The diameter of the sorbent zones that can be obtained using these methods is about 60 μm to about 500 μm. For preferred versions of the present invention, the diameter of the sorbent zone is about 75 μm to 250 μm, and the most preferred diameters are about 100 μm to 200 μm.

In view of the microscale dimensions of sorbent zones, it is desirable to maximize the amount of the analyte binding partner immobilized within these regions. Moreover, the conditions to maximally perturb the sample concentration by harvesting the entire analyte mass dictate a concentration of analyte binding partner that is considerably higher than the $0.01 K^{-1}$ value suggested by "ambient analyte" theory. Generally, a molar excess of analyte binding partner to analyte is preferred. Since the mass of an analyte present in a clinical sample will typically be in the range of about $10^5$ to about $10^{10}$ molecules per 100 μl sample, at least about $10^5$ molecules and preferably as high as $10^{12}$ molecules of analyte binding partner will be immobilized within a sorbent zone. Theoretically, a maximum number of analyte binding molecules would be reached when steric effects begin to dominate. The most preferred version of the present invention has about $10^{10}$ to about $10^{11}$ molecules of analyte binding partner immobilized within a sorbent zone having a diameter of about 100 μm to about 200 μm.

V. Arrays

Arrays can consist of sorbent zones of any number, pattern, design, or geometry, e.g., circles, lines, or an n×n number of spots. Preferably, arrays are an n×m matrix of sorbent zones, wherein n is the number of columns and m is the number of rows. The total number of columns and rows can be adapted as needed to a particular application. Adequate spacing between the sorbent zones is desirable to prevent cross contamination by assay reagents and to facilitate accurate image detection. In a preferred version of the present invention the sorbent zones are aligned in a matrix, wherein the vertical and/or horizontal space between sorbent zones is about 500 μm.

Multianalyte binding assays can be conducted by constructing an array having a plurality of sorbent zones, wherein the sorbent zones are divided into subsets of sorbent zones. Each subset of sorbent zones can have different analyte binding partners immobilized within the sorbent zones of the subset. The subsets may contain identical sorbent zones for the purpose of determining mean values and sampling error. Alternatively, subsets having identical sorbent zones can be used to provide a dose response curve for a particular analyte. Different subsets of sorbent zones having different analyte binding partners can be used to detect and quantify different analytes from the same sample. A preferred version of a multianalyte binding assay, which utilizes an array having subsets of sorbents zones is described in Example III of the present application. In the Example, there are four subsets of sorbent zones. Each subset has five identical sorbent zones, which carry the same monoclonal antibody to a single IgG subtype. Moreover, each subset of five identical sorbent zones utilizes a different monoclonal antibody, each monoclonal antibody recognizing one of four different IgG subtypes.

As will be apparent to one of skill in the art, a variety of different multianalyte binding arrays can be constructed to suit the particular purpose at hand. For example, a blood sample can be screened for the presence of antibody or antigens indicative of a variety of infectious agents, such hepatitis and human immunodeficiency viruses.

VI. Fluorescent Labels

The analyte mass harvested by the binding assay is tagged with a fluorescent label for detection. Although any fluorescent dye may be suitable, dyes that absorb and emit radiation within the near infrared (NIR) region of the electromagnetic spectrum are preferred. The benefits of using NIR fluorescent dyes as labels include:

(1) there is very low interference at the NIR wavelength of about 650 to 1000 nm where only a few classes of compounds exhibit significant absorption or fluorescence;
(2) NIR fluorescent dyes are compatible with the use inexpensive gallium-aluminum-arsenide (Ga—Al—As) semiconductor laser diodes to induce fluorescence; and (3) NIR detection permits flexibility in selecting silicon photodetectors.

Compounds that possess absorbance at the lower NIR (650–750 nm) include phthalocyanine and napthalocyanine dyes, metal complex dyes, triphenyl- or diphenylmethanes, azo dyes, quinones, and carbocyanine dyes. To our knowledge, only one readily available group of molecules, tricarbocyanine dyes, are fluorescent in the higher NIR (750 nm and above). The large molar extinction coefficients and high quantum efficiencies of the cyanine dyes make them good candidates for applications using laser induced fluorescence.

The most preferred cyanine dyes are the phthalocayanine, dicarbocyanine and tricarbocyanine dyes, including La Jolla Blue, Cy5, BCy5, DBCy5, Cy7, BCy7, and DBCy7. The dyes are commercially available from Molecular Probes (Eugene, Oreg.) and Amersham (Buckinghamshire, UK).

In a preferred version of the present invention, the harvested analyte is tagged by attaching a labeled binding partner, as in the well known "sandwich assays" of the prior art. Methods of attaching fluorescent dyes to binding partners, such as oligonucleotides, receptors, or antibodies are also well known in the art. In such a "sandwich assay," the labeled binding partner preferably binds to a portion of the analyte that is not bound to immobilized analyte binding partner. A most preferred version of the present invention utilizes an antibody labeled with DBCy5 as the labeled binding partner.

VII Kits

Kits may be conveniently assembled for use in conjuntion with the binding assay of the present invention. The kit will contain a substrate having an array of sorbent zones, preferably a multianalyte binding array, for harvesting analytes from a sample. In addition, kits may include at least one container having a labeled binding partner, for tagging the captured analytes. Moreover, kits may include standard reagents, such as positive and negative controls, or pre-measured analytes for dose response curves. Such kits may also include buffers and blocking solutions that are often used for intermediate assay steps, which reduce non-specific binding of sorbent materials.

VIII Immobilization

The array of sorbent zones of the present invention can be created by simple pipetting, by jet printing or photolithography. Although photolinking the sorbent materials though a mask may prove to be a superior method of fabricating an array within narrow tolerances, at present thermal/piezo jet printing is the method of choice for localizing sorbent zones. The sorbent materials of the present invention, such as the first binding partner, conjugate, or analyte binding partner, are dispensed in droplets of about 60 pl to about 1 nl and dry rapidly, generally within 30 seconds.

Preferably, the first set of sorbent materials dispensed on the substrate are attached covalently. Methods for covalently attaching binding partners, such as oligonucleotides, receptors, and antibodies, to plastics materials is well known in the art. A preferred method of covalently attaching the first binding partner or analyte binding partner to the substrate utilizes a photoactive linker molecule, such as the Photo-Link® Technology commercially available from SurModics, Inc. (Eden Prairie, Minn.). The binding partner is derivatized with a photoactive linker, deposited on the substrate, and the dry spots are immobilized by UV irradiation. The covalent linkage of binding partners to the substrate eliminates depletion of the sorbent materials during subsequent washing steps and maximizes the signal generated from captured analyte.

IX Analyte Capture & Labeling

Conditions for harvesting most of the analyte from a sample volume can be optimized by the following factors: (1) utilizing sorbent materials having high affinity constants, e.g. $K_A > 10^{10}$ liter mole$^{-1}$, to give stronger binding; (2) minimizing the sample volume; and (3) utilizing a large initial mass of analyte binding partner as a capture reagent. However, such optimization efforts are subject to "real world" limitations. For example, the affinity constants of commercially available binding partners directed to an analyte of interest may be less than optimal. Moreover, the sample volume cannot be decreased indefinitely without reducing the number of analyte molecules below a detectable level. In preferred versions of the present invention, we have found sample volumes from about 20 µl to about 500 µl to be suitable for analyte capture and detection. Finally, the initial mass of a capture reagent cannot be increased infinitely, because steric effects eventually dominate.

Under the ideal assay conditions for harvesting analyte discussed above, our theoretical estimates indicate that at least about 60% of the analyte will be captured by a high affinity binding partner having a $K_A > 10^{10}$ liter mole$^{-1}$. This figure is well over the <10% reduction of analyte concentration recommended by Ekins et al. In the mass sensing assay of the present invention, the analyte is substantially depleted from the sample to form an analyte capture complex with a high affininty binding partner.

In a similar manner, the signal obtained from the tagged analyte capture complex can be optimized by the use of a labeled binding partner having a relatively high affinity constant. Moreover, the signal may be further enhanced if a plurality of fluorescent dye molecules are attached to the specific binding partner. For example, the DBCy5-labeled antibody used in the following examples had about 2.8 molecules of DBCy5 per antibody molecule.

In practice, however, problems may arise when non-specific binding contributes a higher noise level, thereby decreasing the sensitivity of the system. In Example III, such problems with high background levels decreased the sensitivity of the assay to about $10^8$ molecules of analyte. Fortunately, this is within limits suitable for many clinical applications. Further optimization efforts to reduce non-specific binding will likely increase the sensitivity of the assay closer to a lower limit of about $10^5$ molecules, as in the avidin-biotin model system.

X Illumination

Typically the arrays are illuminated using a laser source to produce laser-induced fluorescence (LIF) of the tagged analyte capture complex. The use of the preferred carbocyanine dyes, which fluoresce in the short wave NIR region between 670 and 900 nm, permits the use of inexpensive solid state GaAlAs diode lasers for excitation. Moreover the cyanine dyes yield emission wavelengths near the optimum radiant sensitivity of silicon detectors.

XI. Image Detection

Imaging detection is preferably performed using a Peltier-cooled CCD detector that affords high throughput advantages over serial scanning techniques, at less cost than confocal optics. Evanescent wave detection is employed to physically separate the source and detector for further background reduction. A more detailed description of the imaging system can be found in the materials and methods section of the following examples. Quantitative analysis of the resulting image data was performed as described earlier in co-pending provisional application Ser. No. 60/065,937, which is incorporated by reference.

EXAMPLES

The following examples demonstrate the practical feasibility of the mass assay methods using a simplified ligand binding system (avidin & biotin), and the extension of the mass sensing micro-array format to single analyte immunoassay of human IgG. Finally, a multianalyte array assay of the four human IgG subclasses is demonstrated.

Materials and Methods

The highly specific binding of biotin by the protein avidin was selected as an optimal ligand binding assay model with binding affinity about $10^{15}$ liter mole$^{-1}$. For this work, a deglycosylated commercial avidin preparation (NeutrAvidin, Pierce Chemical Co., Rockford, Ill.) was employed, although no statistically significant differences in binding capacity, background, or sensitivity were observed when streptavidin or avidin were substituted.

The fluorescent NIR dye chosen for this work, DBCY5, is the dicarbocyanine analog of indocyanine green. The dye was biotinylated by reaction of its N-hydroxysuccinimidyl ester derivative, in excess, with biotin hydrazide. The resulting biotin derivative has an absorbance maximum near 670 nm, with fluorescence emission occurring at 710 nm. The molar absorptivity in aqueous solutions is 200,000 and the quantum efficiency approximately 20%. These spectral properties are essentially unchanged from the unconjugated dye. Assessment of the degree of biotinylation was performed by two methods. The first involved incubating a single aliquot of the product successively in several wells of a commercially prepared avidin-coated microtiter plate (Pierce Chemical Co., Rockford, Ill.), and noting the residual fluorescence of the solution after removal of all biotinylated material. In this manner, it was determined that 70% of the NIR dye molecules in the product were biotinylated. A second procedure involved the conventional assay of biotin using HABA (4-hydroxyazobenzene-2-carboxylic acid, Pierce Chemical Co., Rockford, Ill.) to confirm the absence of unlabeled biotin residues which would reduce sensitivity by blocking avidin sites.

Microscopic reagent zones were prepared by loading the desired reagent solution into a previously disassembled and ultrasonically cleaned printhead unit of a desktop jet printer (Hewlett Packard ThinkJet, Palo Alto, Calif.). A 3"×3" sheet of precleaned polystyrene film having 1 mil thickness (Whatman Inc., Rockland, Mass.) was then taped to tractor paper and loaded into the printer. Film was precleaned by rinsing in absolute methanol and drying using an inert gas jet. The volume dispensed on each activation of a printer jet was determined by printing a predetermined number of droplets of DBCY5 dye solution of known concentration onto film, then rinsing the dye from the film with a known volume of methanol. The fluorescence of the wash solution was then compared to standard solutions of DBCY5 in methanol. Using this method, the mean droplet volume was determined to be 80 picoliters.

Figure 2:
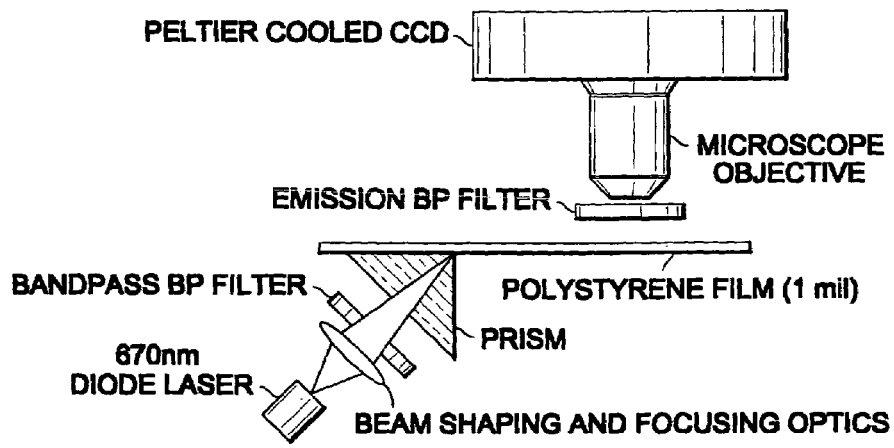
FIG. 2 shows a schematic diagram of the apparatus used for evanescent wave excitation and fluorescence imaging detection.

The experimental apparatus used to measure fluorescence from the printed zones is shown in FIG. 2. Briefly, imaging detection of fluorescence from the microscopic zones was done using a Peltier cooled CCD camera (Princeton Instruments, Inc., Trenton, N.J.) coupled to a 6.5× microscope objective (Melles Griot, Irvine, Calif.) and appropriate excitation and emission filters (Omega Optical filter set XF-48, Omega Optical, Brattleboro, Vt.) to detect isotropic emissions from the film. Evanescent wave excitation of fluorescence from the printed zones was realized by launching filtered emissions at 670 nm from a GaAlAs diode laser (Lasiris, Inc., Quebec, Canada) into the film using a prism coupler of our own design. Quantitative analysis of the resulting 16-bit image data was performed using an automated macro driving the intrinsic functions available in a commercial software package (ImagePro 3.0, Media Cybernetics, Inc., Silver Spring, Md.).

Figure 3:
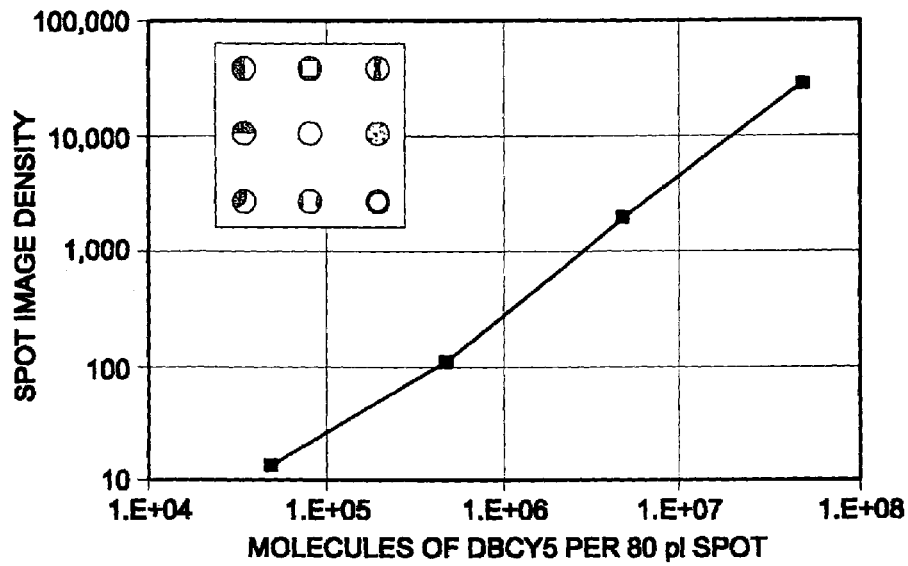
FIG. 3 shows imaging detection of DBCY5 dye printed using solutions of known concentration, which determines precision and detection limits; the inset shows a typical CCD image of a micro-array.

An assessment of the sensitivity and reproducibility of the printing and measurement processes was made by printing standard solutions of underivatized DBCY5 dye, then constructing dose response curves from the reduced image data. As shown by FIG. 3, the imaging system has a mass detection limit of approximately $10^5$ DBCY5 molecules per printed zone. Volumetric precision of the inkjet printer is such that one standard deviation about the mean of spot intensities in a 9-spot array is approximately 6%. The limit of detection is imposed by a background that is a combination of residual spurious long wavelength emission from the diode laser and Raman scattering from the polystyrene film.

Arrays of immobilized avidin spots were prepared by printing a solution of 1 mg/ml NeutrAvidin in buffered solution. This concentration is higher than typically used for the coating of mictotiter plate wells, but is understandable on the basis of the very different volume-to-surface-area characteristics presented by the microscopic experimental scale. The printed spots dry within 30 seconds of deposition, leaving a visible solid residue which permits visible examination of the array and gross verification of printer function. For non-covalent immobilization, a 50 mM carbonate buffer at pH 8.2 was used for printing. For covalent immobilization, the buffer was 50 mM phosphate buffered saline at pH 7.4. Covalent immobilization was achieved by derivatization of NeutrAvidin with a commercial photolabile linker moiety. Following printing of this NeutrAvidin-linker conjugate, covalent immobilization was obtained by exposing the dry printed arrays to light from a UV source (Dymax 2000EC, Torrington, Conn.) for three minutes. Subsequent experience with dry avidin arrays has indicated that these materials are stable under refrigerated vacuum desiccation for at least six months.

Immediately prior to use, printed arrays were washed to remove any loosely bound avidin. This washing was accomplished with "PBS/T", a 0.2% solution of Tween-20 in phosphate buffered saline, pH 7.4. Assay of biotin-DBCY5 was then performed by incubating printed arrays with varying volumes and concentrations of DBCY5-biotin conjugate diluted in PBS/T. Incubation times were varied from 15 minutes to overnight, using a microtiter plate shaker (Lab Line, Inc., Melrose Park, Ill.) or rotating wheel (Glas-Col, Terre Haute, Ind.) depending on the sample volume under study. Following the incubation, the PBS/T wash was repeated to remove free DBCY5 and/or loosely bound DBCY5-biotin. A final rinse in deionized water was performed to remove buffer salts from the film prior to drying. The arrays were then dried using an inert gas duster and imaged within one hour for quantitative analysis.

Immunoassay of the human IgG subclasses was performed using biotinylated monoclonal antibodies (clones HP-6091, HP-6014, HP-6050, and HP6025, Sigma Chemical Co., St. Louis, Mo.) by a protocol derived from that of Hamilton, et al. {"Monoclonal antibody-based immunoenzymetric assays for quantification of human IgG and its four subclasses." *J. Immunoassay* 9:275–296 (1988)}. Antibody arrays were generated either by incubation of avidin printed arrays with an excess of biotinylated capture antibody, or by direct jet printing of antibody to form multianalyte arrays. The arrays were then washed and blocked with a 5 mg/ml solution of BSA in PBS, and incubated for three hours with 50 microliters of solution containing human myeloma proteins (Sigma Chemical Co., St. Louis, Mo.) diluted in 1 mg/ml BSA. Arrays were then washed, and incubated for one hour with polyclonal mouse anti-human IgG (Jackson Immunoresearch, West Grove, Pa.) labeled with approximately 2.8 DBCY5 molecules per antibody. Finally, the arrays were washed, dried, and imaged as done in the avidin/biotin system.

Example I

Biotin/Avidin Binding System

Figure 4:
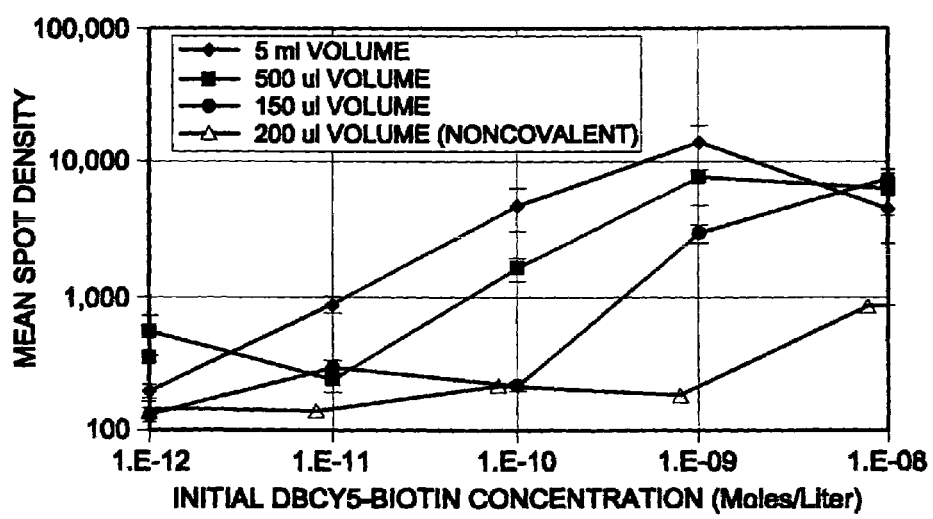
FIG. 4 shows dose response data for DBCY5-biotin incubated with avidin micro-arrays; the data show dependence on the volume of the sample during incubation; noncovalent adsorption of avidin to polystyrene film yields low signals.
Figure 5A:
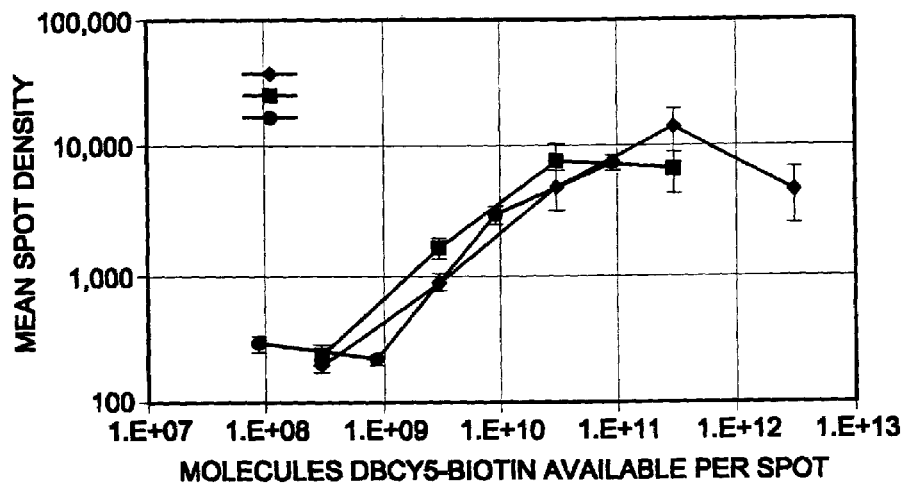
FIG. 5A shows the data from FIG. 4 plotted versus DBCY5-biotin mass present, the replotted dose response data indicate that the micro-array senses analyte mass rather than concentration, i.e., analyte "harvesting" is taking place.
Figure 5B:
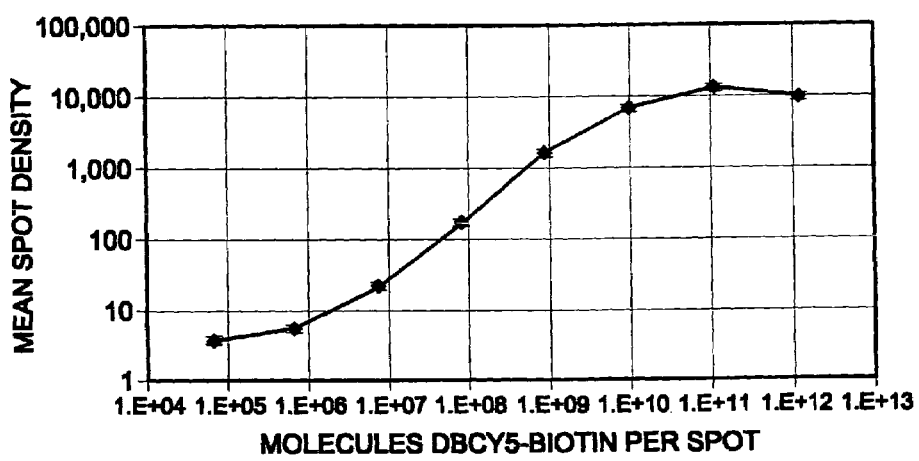
FIG. 5B shows a dose response curve for a 200 microliter volume of DBCY5-biotin, indicating a mass detection limit for the avidin-biotin system of approximately $10^6$ molecules per spot (error bars indicate one standard deviation about the mean density of a 9-spot array)

FIG. 4 shows typical dose response curve results obtained by titration of 9-spot avidin arrays with four different fixed volumes of DBCY5-biotin solution prepared by serial dilution. The mean CCD pixel intensity computed from the imaged fluorescent spots tracks dye-biotin concentration in the quantitative manner expected from conventional binding assays. The data in FIG. 4 reflects one hour incubation time: although signal was observed to increase with incubation times from 30 minutes to 3 hours, signals after 15 hours of incubation were found to be only slightly higher than after three hours. A standard incubation time of three hours was therefore adopted for maximum sensitivity (FIG. 5*b*).

In the mass sensing micro-assay format, maximization of signal is achieved by maximizing the functional analyte binding capacity per unit area. Dose response curves from noncovalently immobilized avidin arrays exhibit a relatively low density of binding sites relative to covalent attachment (FIG. 4). Noncovalent immobilization was also found to be susceptible to desorption and loss of capture reagent during wash steps with surfactant (0.2% Tween-20, Pierce Chemical CO., Rockford, Ill.) present. These results have led to the abandonment of noncovalent attachment in favor of covalent immobilization methods. Using covalent immobilization, signal losses in wash steps have been found to be insignificant, and we believe that retention of bound analyte on the printed arrays is facilitated by the high local concentration of binding sites experienced by bound species.

Atomic force microscopy of an immobilized avidin spot after washing indicates that the covalent printed array spots have an irregular topology extending up to 200 nm vertically from the surface of the film. Integration of the AFM topology data indicates that the dry residue composing one "spot" has a volume on the order of $6\times10^{-11}$ cm$^3$, placing an upper limit on the mass of avidin of roughly 190 picograms per spot assuming each avidin molecule occupies 6 nm$^3$ in the dry matrix. Since approximately 100 picograms of avidin was deposited per spot in the AFM study (100 picoliters of 1 mg/ml solution), the AFM experiments indicate that most of the avidin mass actually printed is covalently incorporated into the spot "structure". The printed avidin spots in the AFM study were titrated with DBCY5-biotin solutions of known concentration and found to have a binding capacity on the order of $10^9$ dye-biotin molecules per spot, equivalent to roughly 100 picograms of avidin per spot assuming one binding site per avidin molecule. This result, together with the AFM data, implies that between one and two active sites are present per avidin molecule after printing and immobilization. Note that the signal levels in FIG. 3 result from higher laser power and cannot be used to quantify binding capacity by comparison with FIGS. 5a and 5b.

If the printed volume is increased from 100 picoliters to 1 nanoliter, the spot diameter roughly doubles, to 200 microns. Titration of these larger spots with DBCY5-biotin then indicates a functional binding capacity on the order of $10^{10}$ dye-biotin molecules bound per printed spot, or roughly 3500 ng/cm$^2$, assuming one binding site active per avidin molecule. This binding site density is roughly 20 times higher than the 130 to 150 ng/cm$^2$ typically specified for commercial avidin-coated polystyrene microtiter plates, probably because of the complex topology of the printed spots.

The inflection points of the titration curves obtained from these 200 micron spots show dependence on the volume of the dye-biotin solution present during the three hour incubation (FIG. 4). As the volume of dye solution in contact with the arrays is increased from 150 microliters to 5 milliliters, the titration curve shifts along the dye-biotin concentration axis toward lower concentrations. If the data are plotted as a function of the total analyte mass present, rather than concentration, the data are found to agree to within the standard deviation about the mean pixel image intensity of the nine spots in each array (FIG. 5). The printed avidin arrays respond to analyte mass, not to concentration, because they have sufficient affinity and binding capacity to significantly deplete the solution of dye-biotin as the solution volume is reduced. The functional detection limit for DBCY5-biotin can be arbitrarily defined as the dye-biotin concentration that yields a mean spot fluorescence intensity in a 9-spot array at least 3 standard deviations above the mean of a "blank" array incubated for three hours with standard PBS/0.2% Tween solution. This functional detection limit is encountered when the initial dye-biotin solution provides a mass on the order of $10^5$ molecules of dye-biotin per spot. This limitation is imposed by the spectroscopic background characteristic of the instrumentation used, as indicated in FIG. 3.

Figure 6:
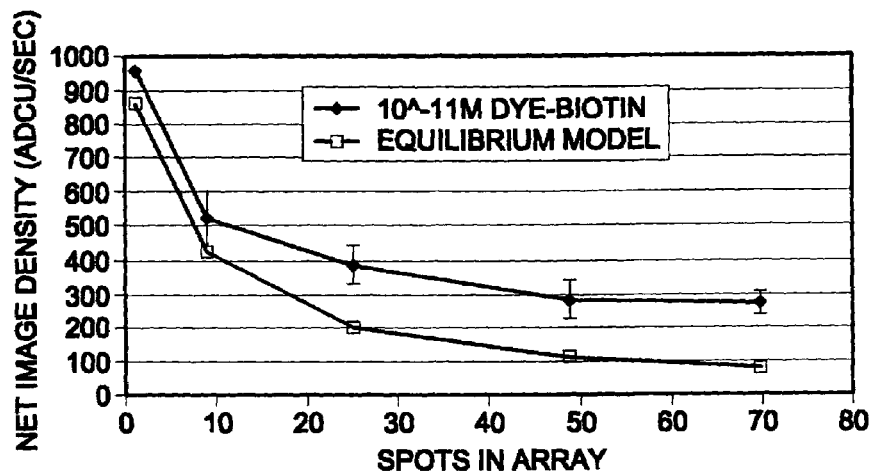
FIG. 6 shows reducing the number of spots gives increasing signal—further evidence of harvesting; computation using an equilibrium model indicates that any kinetic limitation is minor.

If the number of avidin spots per array is varied in such a mass-sensing array, the law of mass action would imply that the density of analyte bound per spot should vary inversely with the number of spots present. When fewer spots are printed per array, the total analyte mass present during incubation is collected onto fewer spots, leading to increased signal from any one spot. FIG. 6 shows experimental results from three hour incubations in which 100 microliter aliquots of $5\times10^{-10}$M DBCY5-biotin solution were in contact with arrays having 1, 9, 25, 49, or 70 spots. Also shown on the plot is the signal predicted by quadratic solution of the mass action law, assuming an affinity constant for avidin of $10^{15}$M$^{-1}$ a binding capacity of $10^{10}$ biotin-dye molecules per spot, and a mean fluorescence image intensity of $10^4$ at binding site saturation (compare FIG. 5). The experiment confirms the mass-sensitive nature of the avidin arrays, and also indicates that the three hour incubation gives results comparable to those expected based on thermodynamic considerations alone. Microscopic diffusive transport of biotin-DBCY5 from bulk solution to the printed spots is apparently rapid enough for practical micro-array assays to operate in a mass-sensing regime while using conventional incubation times on the order of one to several hours.

Example II

Assay of Human IgG3

Figure 7:
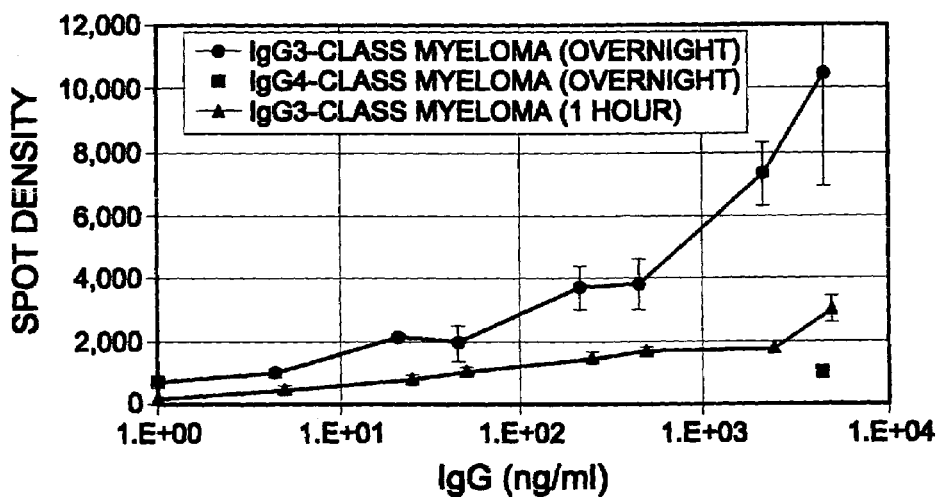
FIG. 7 shows dose response curves for a IgG3 micro-array assay; specificity is observed for the IgG3 subclass relative to a control experiment with IgG4-class myeloma (data from a 3 hour incubation would lie within the indicated intra-aray standard error for the overnight incubations)

The avidin-biotin system described was extended to the assay of human IgG3 by incubation of standard printed avidin arrays with an excess of biotinylated HP-6050 monoclonal antibody specific for the IgG3 subclass, using the assay protocol described in the experimental section. FIG. 7 shows a dose response curve resulting from assay of 50 microliter aliquots of human myeloma proteins (kappa chain). Subclass-specific response to IgG3 is observed, based on negative control experiments using solutions of human myeloma proteins of different subclasses. An overnight sample incubation was found to yield insignificant signal gains over a three hour incubation, and incubation for one hour resulted in a three-fold reduction in overall signal levels, but no loss in sensitivity. The detection limit for IgG3 (arbitrarily defined as the interpolated IgG concentration at which image density of the spots in the array is three standard deviations greater than a "blank" experiment) was approximately 15 ng/ml, a concentration providing about $3\times10^8$ molecules of IgG3 per array spot. A conventional ELISA plate assay has been reported by Hamilton et al. to have a sensitivity of 2 ng/ml, using a monoclonal antibody having an 8-fold higher affinity for IgG3 (HP-6047. Based on equilibrium considerations, a micro-array IgG3 assay employing the higher affinity antibody should demonstrate sensitivity comparable to the ELISA, despite the use of direct fluorescence. We attribute this level of sensitivity to the harvesting of analyte mass from bulk solution, concentrating the analyte on the printed spots to a degree that removes the need for an enzyme/substrate amplification system and permits use of the simpler direct fluorescence labeling. The limit of detection in the IgG3 assay is imposed by immunochemical nonspecific binding, which is observed to occur only to the printed spots rather than the blocked, untreated polystyrene areas between the arrays. The nonspecific binding background signal is approximately 1000 times the instrumental detection limit observed for the avidin-biotin system (FIG. 8), implying that the micro-array technique is capable of greater sensitivity if the nonspecific binding is reduced below the level encountered in the IgG3 assay.

Figure 8:
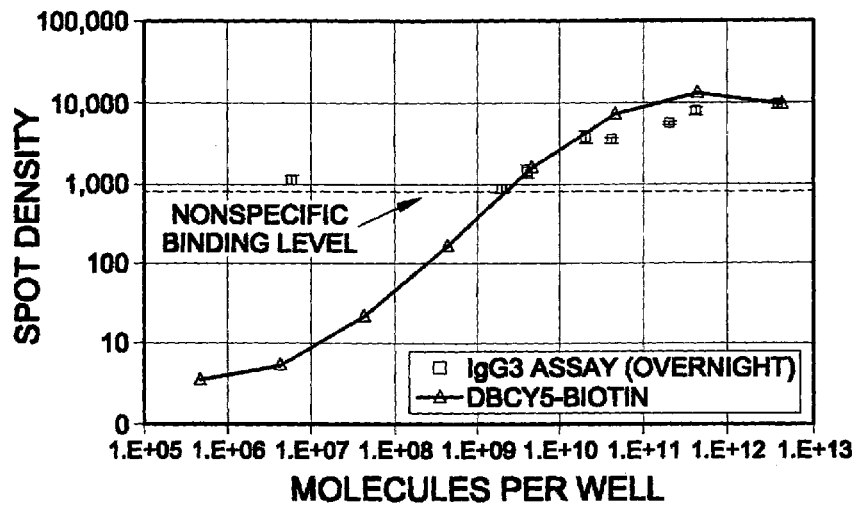
FIG. 8 shows dose response curves of the IgG3 assay and the avidin-biotin system plotted against mass units; there is a limitation due to nonspecific binding on the IgG3 assay, but approximate agreement along linear portions of both curves approaching the maximum signal levels.

The maximum signal levels observed in the IgG3 dose response data are comparable to those measured in the dye-biotin system (FIG. 8). Apparently any steric constraints which limit the access of antibody reagents to the avidin binding sites is offset by the use of multiple fluorescent labels on the polyclonal probe antibody. The IgG3 and avidin/biotin dose response data also have similar shape when plotted versus total number of analyte molecules per well, neglecting the assay's nonspecific binding level. This agreement is consistent with the immunoassay's operation in the mass sensing regime, despite the reduced affinity ($10^8 M^{-1}$) when compared to the avidin/biotin system.

Example III

Multianalyte Immunoassay of the Four Human IgG Subclasses

Figure 9:
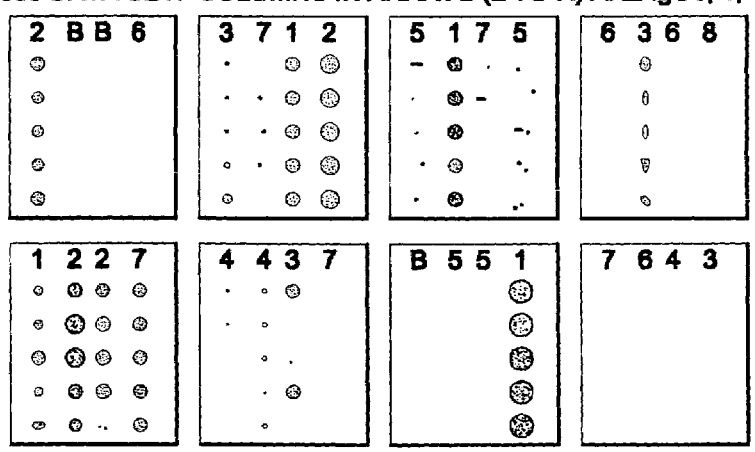
FIG. 9 shows raw image data from the four-analyte human subclass assay; numbers over each micro-array column indicate the number of serial dilutions performed for each subclass during preparation of the four-component mixture assayed in a given image ("B" indicates blank)
Figure 10A:
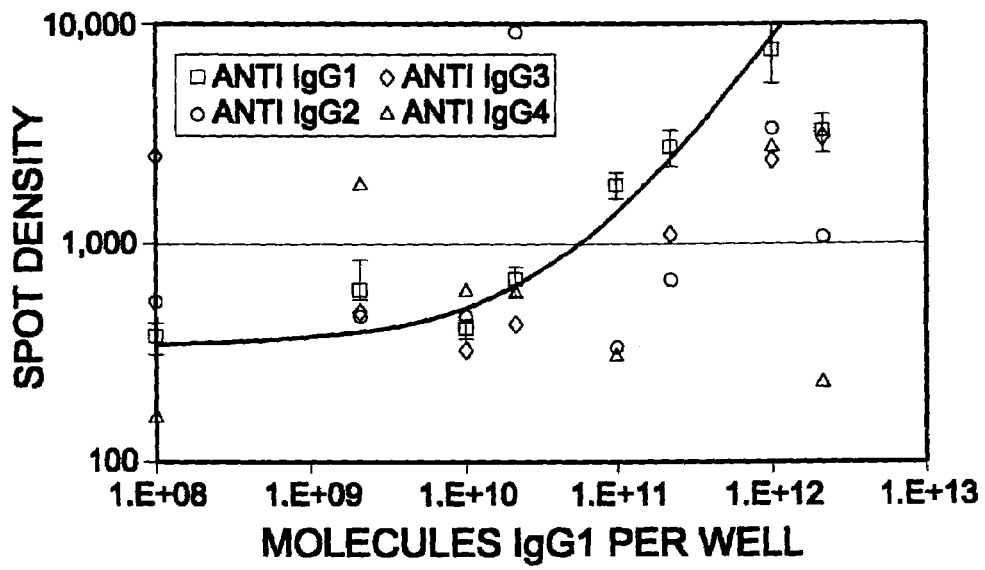
FIG. 10 shows dose responses for the four human subclasses assayed simultaneously for each of eight "random" mixtures of human myeloma proteins.
Figure 10B:
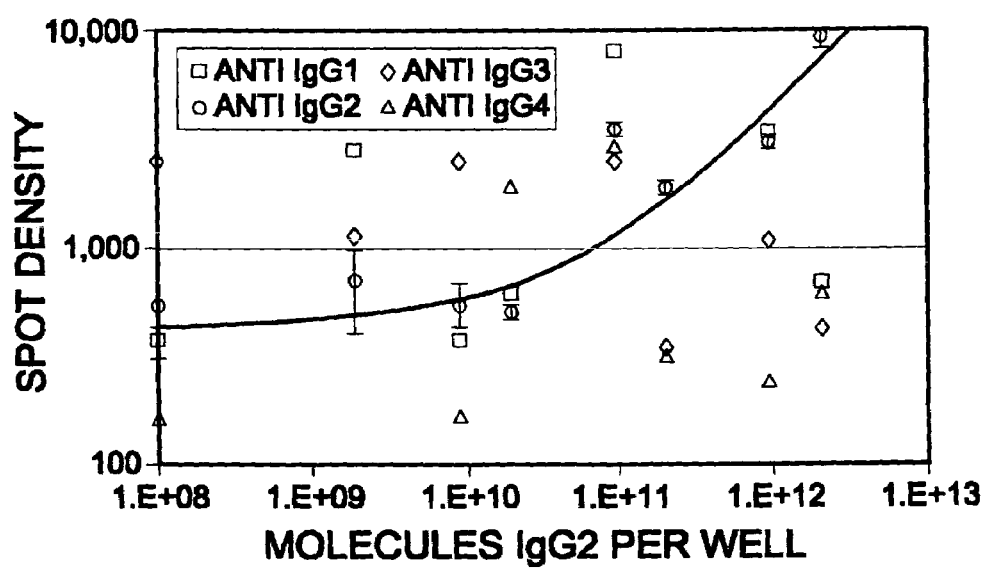
Figure 10C:
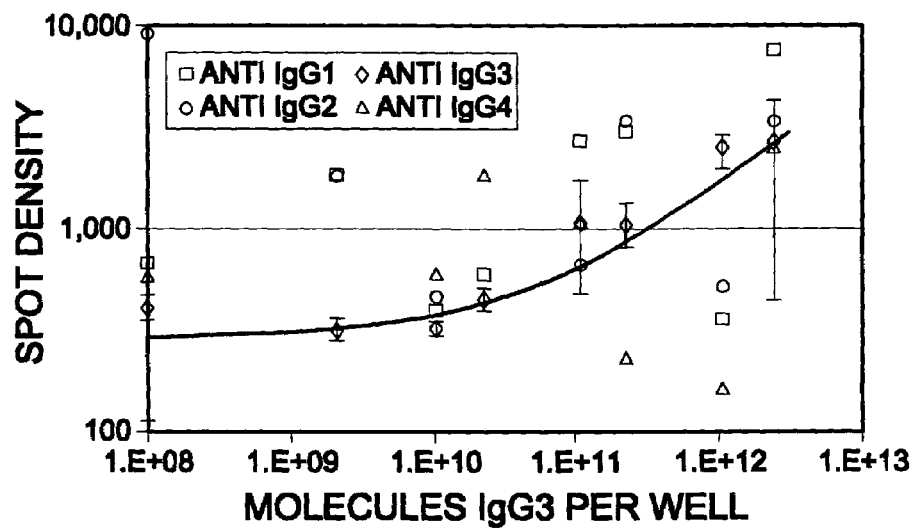
Figure 10D:
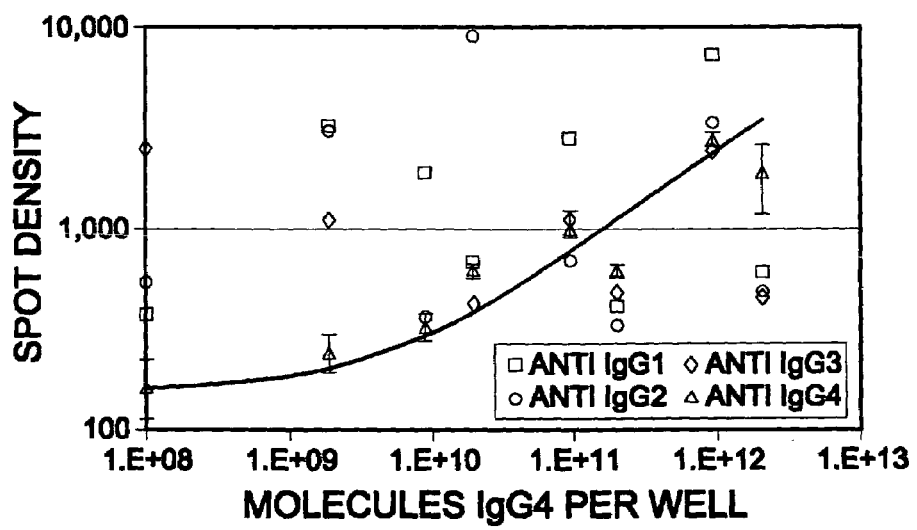

Extension of the IgG3 assay to a multianalyte array assay of all four human IgG subclasses was performed by jet printing of a 1 mg/ml biotinylated monoclonal antibody solution to form arrays in which each column of 200 micron spots recognize a different IgG subclass. Each spot was generated using 1 nanoliter of solution. Eight different mixtures of human myeloma proteins from each subclass were prepared in PBS solution with 5 mg/ml BSA and assayed using the same protocol developed for assay of IgG3. The mixtures assayed included pseudo-random combinations of myeloma concentrations between 10 micrograms $ml^{-1}$ and 10 ng $ml^{-1}$, as well as mixtures in which one subclass was not present. Following the sample incubation and washing, the DBCY5-labeled polyclonal mouse anti-human IgG reagent was then used to develop signal from all four assays simultaneously. The image data for the four-analyte array (FIG. 9) shows qualitative dependence between spot intensity along each column and the expected concentration of the appropriate myeloma subclass in the 50 microliter IgG mixture aliquots assayed. Quantitative image processing yields dose response curves (FIG. 10) for each IgG subclass if fluorescence from the appropriate column of the micro-array is plotted against the myeloma protein concentrations in the mixtures. Detection limits may be crudely estimated from the dose response data and appear to be similar to the 10–20 ng/ml observed in the single-component IgG3 assay.

Evidence for subclass specificity is seen in the poor correlations observed if data from a micro-array column is plotted versus myeloma concentrations for the incorrect subclass. Multilinear regression on the multianalyte array data indicates that any cross reactivity between the assays is sufficiently small as to be obscured by the spot-to-spot variability within the columns. This error is currently 10 to 15% of the mean intensity in one column (one standard deviation) owing to mechanical difficulties encountered in the jet printing of multiple analytes. The low level of cross reactivity indicates that antibody specificity can be retained despite the rigors of jet printing and drying. Stability of dry printed multianalyte arrays has been shown to be dependent on the particular antibodies immobilized, but has been demonstrated to exceed one month if arrays are stored in a refrigerated vacuum desiccator and coated with a commercial immunoassay stabilizer preparation (StableCoat, SurModics Inc., Eden Prairie, Minn.).

That this multianalyte array assay senses each analyte's mass rather than its concentration can be shown by preparation of micro-arrays containing columns of spots specific for IgG3, IgG4, with some arrays also containing a third monoclonal recognizing both IgG3 and IgG4 (clone HP6017, Sigma Chemical Co., St. Louis, Mo.). These experiments demonstrate intra-array competition, with the IgG3 and IgG4 signals being reduced, relative to controls, in the presence of the spots recognizing "total" IgG. This effect would not be seen if the sample solution in contact with the array were not being depleted of analyte, and confirms that signal levels in the multianalyte array assay are being enhanced by "harvesting" and concentration of the analyte on the printed spots. Intra-array competition must be taken into account in mass-sensing multianalyte arrays designed to sense total IgG in addition to the subclasses.

Although the mass-sensing micro-array assay format depends on a high density of binding sites, the extremely small scales involved lead to an overall decrease in the mass of antibody required per test. Approximately 1 ng of antibody is deposited per spot in the printed arrays, compared to the 100 ng typically immobilized in one well of a 96-well microtiter plate. The actual savings in reagent may be even greater than this because as much as several micrograms of antibody are often added per well during (noncovalent) plate coating to yield a "securely" bound antibody mass of 100 ng per well. This potential cost savings may be important in many applications.

CONCLUSIONS

It has been shown that jet printed spots of reagent having diameters of 100 to 200 microns can be prepared using solutions of avidin or antibodies which retain specificity and affinity for their targets. When binding site density is maximized, and binding sites are present in excess, the spots can effectively deplete analyte from bulk solution to yield high local analyte concentration on the printed spot. This "harvesting" of analytes maximizes signal to background ratios, and permits the detection of $10^5$ or fewer analyte molecules by direct fluorescence detection, without resort to enzyme amplification. In this regime, the detected signal depends upon the total analyte mass in a sample, rather than its concentration. Once analyte molecules are bound by the micro-array, they are quite resistant to loss during wash steps, evidently because they experience a high local concentration of binding sites. A simple immunoassay of IgG3 using the mass-sensing micro-array approach has demonstrated sensitivity equal to a conventional ELISA plate assay, and has been extended to a simultaneous multianalyte assay of the four human IgG subclasses in a single 50 microliter sample aliquot. Detection limits of the micro-array assay are consistent with the published sensitivity of conventional plate assays using similar immuno-reagents and protocols, despite the fact that the micro-array approach requires as little as 1/1000the antibody mass of conventional microtiter plate assays using coated wells.

Although the present invention has been described in considerable detail with reference to certain preferred versions thereof, other versions are possible. Therefore the spirit and scope of the appended claims should not be limited to the preferred versions contained herein.

We claim:

1. A binding assay for sensing analyte mass in a liquid sample, comprising:

a) immobilizing an array on a surface of a substrate, wherein the array comprises a plurality of microscopic sorbent zones, wherein a microscopic sorbent zone comprises a multi-layer matrix of an analyte binding partner, the matrix extending up to 200 nm vertically from the surface of the substrate;

b) contacting a defined volume of sample believed to contain an analyte with at least one microscopic sorbent zone, the analyte binding partner in the microscopic sorbent zone being present in excess relative to the analyte, so that any analyte present in the defined volume is substantially depleted from the sample and concentrated on the microscopic sorbent zone to form an analyte capture complex with the analyte binding partner;

c) tagging the analyte capture complex with a fluorescent label;

d) illuminating the microscopic sorbent zone with a laser in the absence of liquid; and e) detecting fluorescence emissions from any microscopic sorbent zone having an analyte capture complex tagged with a fluorescent label, thereby determining the analyte mass harvested from the defined volume of sample, wherein said analyte mass is determined from a dose response curve.

2. An assay according to claim 1 wherein the substrate is a film, sheet, strip, particle, or microtiter plate.

3. An assay according to claim 1 wherein the analyte binding partner is immobilized by covalent binding to the substrate.

4. The assay of claim 3, wherein the immobilizing step a) further comprises:
 a1) derivatizing the binding partner with a photolabile linker moiety to obtain a derivatized binding partner;
 a2) drying the derivatized binding partner on the substrate; and
 a3) exposing the substrate to UV radiation.

5. An assay according to claim 1, the sorbent zones further comprising a first binding partner attached to the substrate, the first binding partner forming a first binding complex with a conjugate, the conjugate comprising a first ligand and the analyte binding partner, wherein the first ligand binds specifically with the first binding partner and the analyte binding partner can bind specifically with the analyte.

6. An assay according to claim 5 wherein the first binding partner is avidin or streptavidin and the first ligand is biotin.

7. An assay according to claim 6 wherein the conjugate is biotinylated antibody.

8. An assay according to claim 5 wherein the first binding partner is immobilized by covalent attachment to the substrate.

9. An assay according to claim 1 wherein the tagging step further comprises: incubating the analyte capture complex with a labeled binding partner, the labeled binding partner having a fluorescent label and being capable of binding to the analyte capture complex.

10. An assay according to claim 9 wherein the labeled binding partner comprises an antibody.

11. An assay according to claim 1 wherein the fluorescent label is a cyanine dye.

12. An assay according to claim 11 wherein the cyanine dye is selected from the group consisting of La Jolla Blue, Cy5, BCy5, DBCy5, Cy7, BCy7, and DBCy7.

13. An assay according to claim 1 wherein the defined volume of sample is from about 20 µl to about 500 µl.

14. An assay according to claim 1 wherein the amount of the analyte binding partner immobilized in a sorbent zone is from $10^5$ to about $10^{12}$ molecules of analyte binding partner.

15. The assay of claim 14, wherein the amount of the analyte binding partner immobilized in the sorbent zone with a diameter from 60 µm to 500 µm is from $10^9$ to $10^{12}$ molecules.

16. An assay according to claim 1 wherein about $10^5$ to about $10^{10}$ molecules of analyte are detected per sorbent zone.

17. An assay according to claim 1 wherein, the diameter of the sorbent zones is about 60 µm to about 500 µm.

18. An assay according to claim 1 wherein the analyte binding partner is an antigen, antibody, oligonucleotide, or receptor.

19. An assay according to claim 1, wherein the array of sorbent zones comprises a plurality of different analyte binding partners.

20. An assay according to claim 19, the sorbent zones further comprising at least two subsets, wherein a first subset of sorbent zones contains a first analyte binding partner and a second subset of sorbent zones contains a second analyte binding partner.

21. An assay according to claim 1 wherein the immobilizing step further comprises dispensing droplets using a printer jet to form the array of sorbent zones.

22. An assay according to claim 21 wherein the volume of the droplets is about 80 pl to about 1 nl.

23. An assay according to claim 1 wherein the illuminating step is conducted by directing near infrared emissions through a prism coupler, into the substrate, thereby producing evanescent wave excitation of fluorescence.

24. An assay of claim 1, wherein the substrate is made of an insoluble non-porous material.

25. An assay according to claim 24 wherein the substrate is selected from the group consisting of polycarbonate, polystyrene, polyethylene, polypropylene, and polymethylmethacrylate.

26. An assay of claim 1, wherein a binding capacity of the microscopic sorbent zone of 150 µm in diameter is about $10^{10}$ analyte molecules.

27. A binding assay for sensing analyte mass in a liquid sample, comprising:
 a) immobilizing an array on a surface of a substrate, wherein the array comprises a plurality of microscopic sorbent zones, wherein each microscopic sorbent zone comprises a multi-layer matrix of an analyte binding partner, the matrix extending up to 200 nm vertically from the surface of the substrate, wherein the amount of the analyte binding partner immobilized in the sorbent zone with a diameter from 60 µm to 500 µm is from $10^9$ to $10^{12}$ molecules;
 b) contacting a defined volume of sample believed to contain an analyte with at least one microscopic sorbent zone, whereby analyte present in the defined volume in substantially depleted from the sample and concentrated on the microscopic sorbent zone to form an analyte capture complex with the analyte binding partner;
 c) tagging the analyte capture complex with a fluorescent label; and
 d) detecting fluorescence emissions from the microscopic sorbent zone to determine the analyte mass harvested from the defined volume of sample, wherein said analyte mass is determined from a dose response curve.

28. The binding assay of claim 1 or 27, wherein the binding partner is immobilized on the surface of the substrate by covalent immobilization.

29. The binding assay of claim 1 or 27, wherein the binding partner is immobilized on the surface of the substrate by non-covalent immobilization.

30. A binding assay for sensing analyte mass in a liquid sample, comprising:
   a) derivatizing a binding partner with a photolabile linker moiety to obtain a derivatized binding partner;
   b) applying aliquots of the derivatized binding partner to a substrate;
   c) exposing the substrate to UV radiation to immobilize the analyte binding partner, whereby an array of microscopic sorbent zones comprising the analyte binding partner forms;
   d) contacting a defined volume of sample believed to contain an analyte with at least one microscopic sorbent zone, the analyte binding partner in the microscopic sorbent zone being present in excess relative to the analyte, so that any analyte present in the defined volume is substantially depleted from the sample and concentrated on the microscopic sorbent zone to form an analyte capture complex with the analyte binding partner;
   e) tagging the analyte capture complex with a fluorescent label;
   f) illuminating the microscopic sorbent zone with a laser in the absence of liquid; and
   g) detecting fluorescence emissions from any microscopic sorbent zone having an analyte capture complex tagged with a fluorescent label, thereby determining the analyte mass harvested from the defined volume of sample, wherein said analyte mass is determined from a dose response curve.

31. An analyte binding array for harvesting analyte from a liquid sample, the array comprising a plurality of microscopic sorbent zones immobilized on a surface of a substrate, wherein a microscopic sorbent zone comprises a multi-layer matrix of an analyte binding partner that binds an analyte from a sample, the matrix extending up to 200 nm vertically from the surface of the substrate, the analyte binding partner being present in an amount sufficient to substantially deplete the analyte from the sample and concentrate the analyte on the microscopic sorbent zone, the microscopic zone being from about 60 to about 500 μm in diameter and the sample containing about $10^5$ to about $10^{10}$ molecules of analyte per 100 μl of the sample, wherein a volume of the sample is from 20 to 500 μl.

32. An array according to claim 31, wherein the array of sorbent zones comprises a plurality of different analyte binding partners.

33. An array according to claim 32, the sorbent zones further comprising at least two subsets, wherein a first subset of sorbent zones contain a first analyte binding partner and a second subset of sorbent zones contain a second analyte partner.

34. The analyte binding array of claim 31, wherein the amount of the analyte binding partner immobilized in the sorbent zone is from $10^9$ to $10^{12}$ molecules.

35. An analyte binding array for harvesting analyte from a liquid sample, the array comprising a plurality of microscopic sorbent zones immobilized on a surface of a substrate, wherein a microscopic sorbent zone comprises an analyte binding partner that binds an analyte from a sample, the analyte binding partner being present in an amount from $10^9$ to $10^{12}$ molecules per each sorbent zone with a diameter from 60 μm to 500 μm.

36. The analyte binding array of claim 35, wherein the analyte binding partner forms a multi-layer matrix in the sorbent zone, the matrix extending up to 200 nm vertically from the surface of the substrate.

37. The analyte binding array of claim 31 or 35, wherein the binding partner is immobilized on the surface of the substrate by covalent immobilization.

38. The analyte binding array of claim 31 or 35, wherein the binding partner is immobilized on the surface of the substrate by non-covalent immobilization.

39. A kit for use in a binding assay that senses analyte mass in a liquid sample of a defined volume, comprising an analyte binding array and a container comprising labeled binding partner,
   wherein the analyte binding array comprises a plurality of microscopic sorbent zones immobilized on a surface of a substrate, wherein a microscopic sorbent zone comprises a multi-layer matrix of an analyte binding partner, the matrix extending up to 200 nm vertically from the surface of the substrate, the analyte binding partner being present in excess relative to the analyte, so that any analyte present in the defined volume of the sample is substantially depleted from the sample and concentrated on the microscopic sorbent zone to form an analyte capture complex with the analyte binding partner, and
   the labeled binding partner having a fluorescent label and being capable of binding to an analyte bound by an analyte binding partner, wherein said analyte mass is determined from a dose response curve.

40. The kit of claim 39, wherein the amount of the analyte binding partner immobilized in the sorbent zone with a diameter from 60 μm to 500 μm is from $10^9$ to $10^{12}$ molecules.

41. The kit of claim 39, wherein the binding partner is immobilized on the surface of the substrate by covalent immobilization.

42. The kit of claim 39, wherein the binding partner is immobilized on the surface of the substrate by non-covalent immobilization.

* * * * *